US012735756B2

(12) United States Patent
Lee

(10) Patent No.: US 12,735,756 B2
(45) **Date of Patent: *Sep. 15, 2026**

(54) ARTIFICIAL INTELLIGENCE BASED MULTI-DIAGNOSTIC METHOD FOR MOSQUITO-BORNE DISEASES

(71) Applicant: Yoonchae Kayla Lee, Gyeonggi-do (KR)

(72) Inventor: Yoonchae Kayla Lee, Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 19/363,951

(22) Filed: Oct. 21, 2025

(65) Prior Publication Data

US 2026/0132476 A1 May 14, 2026

Related U.S. Application Data

(63) Continuation-in-part of application No. 18/941,352, filed on Nov. 8, 2024, now Pat. No. 12,473,602.

(51) Int. Cl.

| | |
|---|---|
| ***C12Q 1/70*** | (2006.01) |
| ***C12Q 1/6893*** | (2018.01) |
| ***G01N 21/78*** | (2006.01) |
| ***G06T 7/00*** | (2017.01) |
| ***G06T 7/90*** | (2017.01) |

(52) U.S. Cl.
CPC .......... *C12Q 1/701* (2013.01); *C12Q 1/6893* (2013.01); *G01N 21/78* (2013.01); *G06T 7/0012* (2013.01); *G06T 7/90* (2017.01); *C12Q 2600/156* (2013.01); *G06T 2207/10024* (2013.01); *G06T 2207/20084* (2013.01)

(58) Field of Classification Search
CPC ........ C12Q 1/701; C12Q 1/6893; G06T 7/90; G06T 7/0012; G06T 2207/20084; G06T 2207/10024
See application file for complete search history.

(56) References Cited

PUBLICATIONS

Rohaim, M.A. et al. Viruses 12(9):972. (Year: 2020).*
Jaroenram, W. et al. Talanta 249:123375. (Year: 2022).*

* cited by examiner

*Primary Examiner* — Diana B Johannsen
(74) *Attorney, Agent, or Firm* — PLEECHAE IP, LLC

(57) ABSTRACT

In a method for diagnosing dengue fever and malaria, DNA extracted from a sample is added to a composition including a first primer set of nucleotide sequences of SEQ ID Nos. 1 to 6 and a second primer set of nucleotide sequences of SEQ ID Nos. 7 to 11, a loop-mediated isothermal amplification (LAMP) reaction of the DNA is performed to produce a colorimetric change, an image of the reaction tube is captured, the image is analyzed using a trained artificial intelligence model to determine whether the reaction indicates a positive or negative result for Dengue virus or *Plasmodium falciparum.*

11 Claims, 12 Drawing Sheets

Specification includes a Sequence Listing.

FIG. 2A

ATTCCAACAGTGATGGCGTTCCATTTAACCACACGTAACGGAGAACCACACATGATC
F3 F2 FIP
GTCAGCAGACAAGAGAAAGGGAAAAGTCTTCTGTTTAAAACAGAGGATGGCGTGA
LF F1
ACATGTGTACCCTCATGGCCATGGACCTTGGTGAATTGTGTGAAGACACAATCACG
B1 LB
TACAAGTGTCCCCTTCTCAGGCAGAATGAGCCAGAAGACATAGACTGTTGGTGCAA
B2 BIP B3

(SEQ ID NO: 17)

FIG. 2B

TGCGAAAGCATTTGTCTAAAATACTTCCATTAATCAAGAACGAAAGTTAAGGGAGTG
F3 F2 FIP
AAGACGATCAGATACCGTCGTAATCTTAACCATAAACTATGCCGACTAGGTGTTGGA
LF F1
TGAAAGTGTTAAAAATAAAAGTCATCTTTCGAGGTGACTTTTAGATTGCTTCCTTCAG
B1
TACCTTATGAGAAATCAAAGTCTTTGGGTTCTGGGGCGAGTATTCGCGCAAGCGAG
B2 BIP B3

(SEQ ID NO: 18)

FIG. 2C

TTAGTTCGTGAATATGATTTGTCTGGTTAATTCCGATAACGAACGAGATCTTAACCT
F3 F2 FIP
GCTAATTAGCGGCAAATACGATATATTCTTACGTGGGACTGAATTCGGTTGATTTG
LF F1
CTTACTTCGAAGAAAATATTGGGATACGTAACAGTTTCCCTTTCCCTTTTCTACTTA
B1
GTTCGCTTTTCATACTGTTTCTTTTTCGCGTAAGAATGTATTTGCTTGATTGTAAAG
B2 BIP B3

(SEQ ID NO: 19)

ARTIFICIAL INTELLIGENCE BASED MULTI-DIAGNOSTIC METHOD FOR MOSQUITO-BORNE DISEASES

CROSS REFERENCE TO RELATED APPLICATIONS AND CLAIM OF PRIORITY

The present application is a continuation in part of co-pending application Ser. No. 18/941,352 filed Nov. 8, 2024, the entire disclosure of which is incorporated herein by reference for all purposes.

REFERENCE TO AN ELECTRONIC SEQUENCE LISTING

A sequence listing electronically submitted on Oct. 21, 2025 as a XML file named 20251021_LC0962425-CIP_TU_SEQ.XML, created on Oct. 21, 2025, and having a size of 24,649 bytes, is incorporated herein by reference in its entirety.

BACKGROUND

1. Field of the Invention

The present invention relates to a diagnostic method for mosquito-borne diseases, particularly dengue fever and malaria, utilizing artificial intelligence to improve diagnostic accuracy and efficiency.

2. Background of the Invention

The intersection of environmental change and biomedical issues is becoming increasingly important in the face of global warming. Infectious diseases that spread around the world are one of the leading causes of high mortality rates in vulnerable regions. It is necessary to focus on emerging infectious diseases and explore the tools needed to rapidly diagnose and respond to the global health impacts of climate change.

Climate change alters temperature, humidity, and rainfall patterns, which in turn affect the habitats and behaviors of pathogens and vectors such as mosquitoes and ticks. Elevated levels of carbon dioxide, a prominent greenhouse gas, trap heat in the atmosphere, leading to increased temperatures. This warming trend contributes to the melting of polar ice caps, rising sea levels, and unpredictable weather patterns, significantly influencing the proliferation and transmission dynamics of vector-borne diseases. Warmer temperatures accelerate mosquito development, enhance biting rates, and shorten disease incubation periods within mosquitoes. Consequently, regions experiencing rising temperatures face heightened risks of diseases such as malaria, dengue, Zika virus, and yellow fever.

The expansion in the areas in which mosquitoes thrive puts more communities at risk increases the number of months each year that are conducive to disease transmission in places already prone to mosquito-borne diseases. This is not limited only mosquito-borne diseases, as the sudden disease outbreaks and accelerating effects of climate change could lead to the emergence of unpredictable infectious diseases in the future.

Additionally, extreme weather events, such as floods and droughts, can disrupt ecosystems and increase human exposure to pathogens. This combination of environmental changes and evolving pathogens creates a landscape where new and unexpected infectious diseases could emerge, posing significant challenges to public health systems worldwide.

These, for instance, is predominantly concentrated in diseases impose substantial burdens on healthcare systems, particularly in communities with limited resources. Malaria in Africa accounts for approximately 95% of global cases. The disease, caused by the *Plasmodium* parasite and transmitted by female *Anopheles* mosquitoes, manifests in various species including *P. falciparum* and *P. vivax*, with *P. falciparum* being the most lethal. Dengue fever, on the other hand, is widespread in regions such as Southeast Asia and the Americas, but as temperatures rise, these areas may also see an increase in malaria cases.

Dengue infections are caused by four viruses named DEN-1, DEN-2, DEN-3, and DEN-4. The viruses share approximately 65% of the genomes, though there is some genetic variation. Despite these differences, infection with any of the dengue serotypes leads to the same disease and range of clinical symptoms. Although the distributions among the continents were unbalanced, by 2004, the geographical range of the four serotypes had greatly expanded. Today, all four dengue serotypes coexist in tropical and subtropical regions globally.

Malaria and dengue fever share similar symptoms such as fever, chills, headaches, muscle aches, nausea, and vomiting, making accurate diagnosis essential for effective treatment. Vulnerable populations, such as pregnant women, infants, children, individuals with HIV/AIDS, and travelers, are at higher risk of severe outcomes. Prompt and accurate diagnosis is crucial, as untreated *P. falciparum* and *P. vivax* infections can result in severe illness and death within 24 hours.

Treatments for malaria exist. Patients are prescribed medications to kill the malaria parasite. The type and duration of medication are based on the type of parasite. Some parasites are resistant to malaria drugs. Antimalarial drugs for curing malaria include Artemisinin-based combination therapies (ACTs), Atovaquone, Chloroquine, Doxycycline, Mefloquine, Quinine, and Primaquine. There is no specific medicine to treat dengue. Patients who are diagnosed dengue virus are recommended to see a healthcare provider. In order to cure dengue, patients are provided with specific drugs to pain symptoms. Acetaminophen (paracetamol) is commonly used to control pain while other drugs such as ibuprofen and aspirin can increase the risks of bleeding.

SUMMARY

An object of the invention is to provide a multi-diagnostic kit for mosquito-borne diseases. The multi-diagnostic kit allows the simultaneous detection of whether a subject is infected with dengue virus and/or malaria parasites.

The following technical solutions are adopted in the present invention to achieve the object.

The invention provides a multi-diagnostic kit for dengue and malaria, including a reagent composition including a first primer set consisting of the nucleotide sequences of SEQ ID Nos. 1 to 6, and a second primer set consisting of the nucleotide sequences of SEQ ID Nos. 7 to 11.

The multi-diagnostic kit amplifies target DNAs by the method of Loop-mediated Isothermal Amplification (LAMP) as described in FIG. 1. The primer sets of the invention are designed to be suitable for LAMP of the target DNAs.

The first primer set is for detecting dengue viruses that cause dengue fever. The second primer set is for detecting *Plasmodium falciparum* that causes fatal malaria. The reagent composition may optionally include a third primer set with nucleotide sequences of SEQ ID Nos. 12 to 16, which is for detecting *Plasmodium vivax* that causes malaria with relatively mild symptoms.

The reagent composition further includes hydroxy naphthol blue (HNB) as a colorimetric indicator.

The reagent composition further includes betaine for clearer color change by HNB.

The first and second primer sets may be contained in one regent composition or may be contained in a first reagent composition and in a second reagent composition, respectively.

The multi-diagnostic kit individually indicates the infection status of Dengue virus, *Plasmodium falciparum*, and *Plasmodium vivax*.

The invention provides a method for diagnosing dengue and malaria, including: adding DNA extracted from a sample to the reagent composition in the multi-diagnostic kit; and performing loop-mediated isothermal amplification of the DNA.

The amplification is carried out at 60 to 65° C. for 0.5 to 1 hour.

The method further includes checking the color change of the reagent composition.

The sample is a blood, saliva, urine, or tissue.

The multi-diagnostic kit of the present invention enables rapid and accurate detection of dengue virus and malaria parasites by using the specific primer sets.

The loop-mediated isothermal amplification (LAMP) allows for time- and cost-efficient diagnosis of the mosquito-borne diseases in a single-tube.

The multi-diagnostic kit demonstrates high specificity and sensitivity for dengue virus and malaria parasites under isothermal conditions.

Hydroxy Naphthol Blue (HNB) allows for the direct visualization of DNA amplification results without the need for gel electrophoresis or fluorescent dyes. HNB changes color based on the magnesium ion concentration, which decreases as DNA is amplified in the reaction. A successful amplification causes a visible color change from violet to sky blue.

The multi-diagnostic kit exhibits excellent thermal stability, ensuring relatively accurate diagnostic results even in harsh environments.

The multi-diagnostic kit is applicable in regions with high incidences of mosquito-borne disease pandemics including Africa and Latin America.

The multi-diagnostic kit is suitable for long-term storage.

The invention provides a method for diagnosing dengue fever and malaria, the method including: (a) adding DNA extracted from a sample to a composition including a first primer set consisting of nucleotide sequences of SEQ ID Nos. 1 to 6 and a second primer set consisting of nucleotide sequences of SEQ ID Nos. 7 to 11; (b) performing a loop-mediated isothermal amplification (LAMP) reaction of the DNA to produce a colorimetric change; and (c) capturing an image of the reaction tube and analyzing the image using a trained artificial intelligence model to determine whether the reaction indicates a positive or negative result for Dengue virus or *Plasmodium falciparum.*

The composition may further include a third primer set consisting of the nucleotide sequences of SEQ ID Nos. 12 to 16, and wherein the analysis step additionally indicates whether a reaction result for *Plasmodium vivax* is positive or negative.

In one embodiment, the artificial intelligence model is a convolutional neural network trained on labeled images of positive and negative colorimetric reactions.

In one embodiment, the captured image can be analyzed in RGB, HSV, or LAB color space.

In one embodiment, the analysis result can be displayed via a graphical user interface indicating infection status for each pathogen.

In one embodiment, the artificial intelligence model may provide a confidence score representing the probability of infection.

In one embodiment, the image can be captured using a mobile device camera and analyzed locally or through a cloud-based server.

BRIEF DESCRIPTION OF THE DRAWINGS

FIGS. 2A to 2C show detailed primer designs for targeting specific sequence regions of (FIG. 2A) Dengue virus type 2 (SEQ ID No. 17), (FIG. 2B) *Plasmodium falciparum* (SEQ ID No. 18), and (FIG. 2C) *Plasmodium vivax* (SEQ ID No. 19).

In FIG. 4A, plasmid DNA samples for DENV, *P. falciparum*, and *P. vivax* are verified on a 1.5% agarose gel, with visible bands confirming plasmid presence. In FIG. 4B, PCR products amplified using LAMP outer primers for each target are shown, with distinct bands indicating successful amplification.

DETAILED DESCRIPTION OF THE INVENTION

Figure 1:
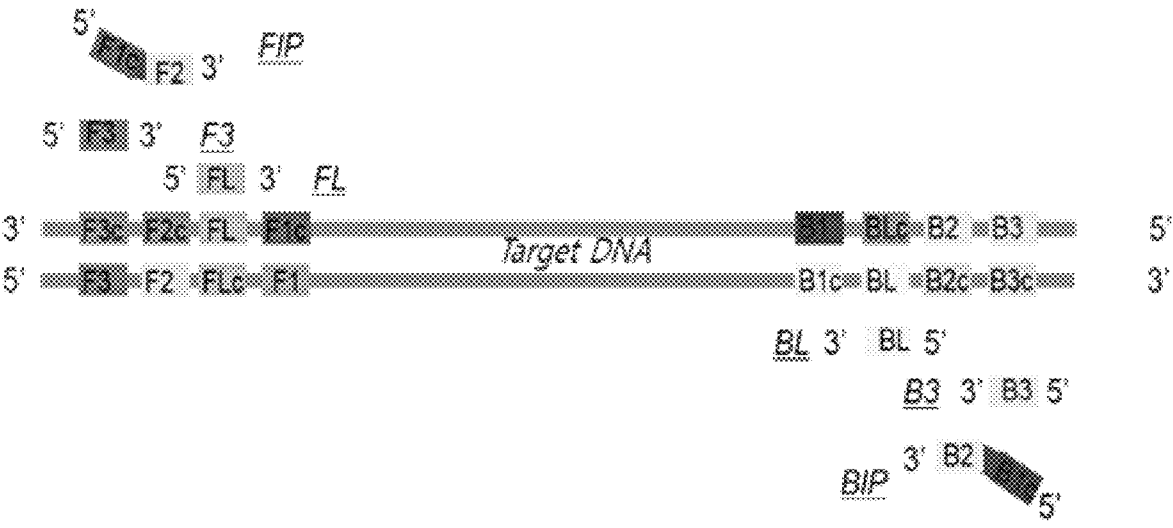
FIG. 1 illustrates the positions of a LAMP primer set (F3, B3, FIP, BIP, FL and BL) corresponding to the target DNA sequence. It shows the locations of each primer in the LAMP process, including: Outer Primers (F3 and B3) which are positioned on the ends of the target sequence and initiate the outer amplification, Internal Primers (FIP and BIP) which consists of sequences that bind to regions inside the target, helping to create the initial loop structure necessary for amplification, and Loop Primers (FL and BL) which bind to the single-stranded loop regions created by the internal primers, enhancing the speed and efficiency of the amplification reaction.
Figure 3:
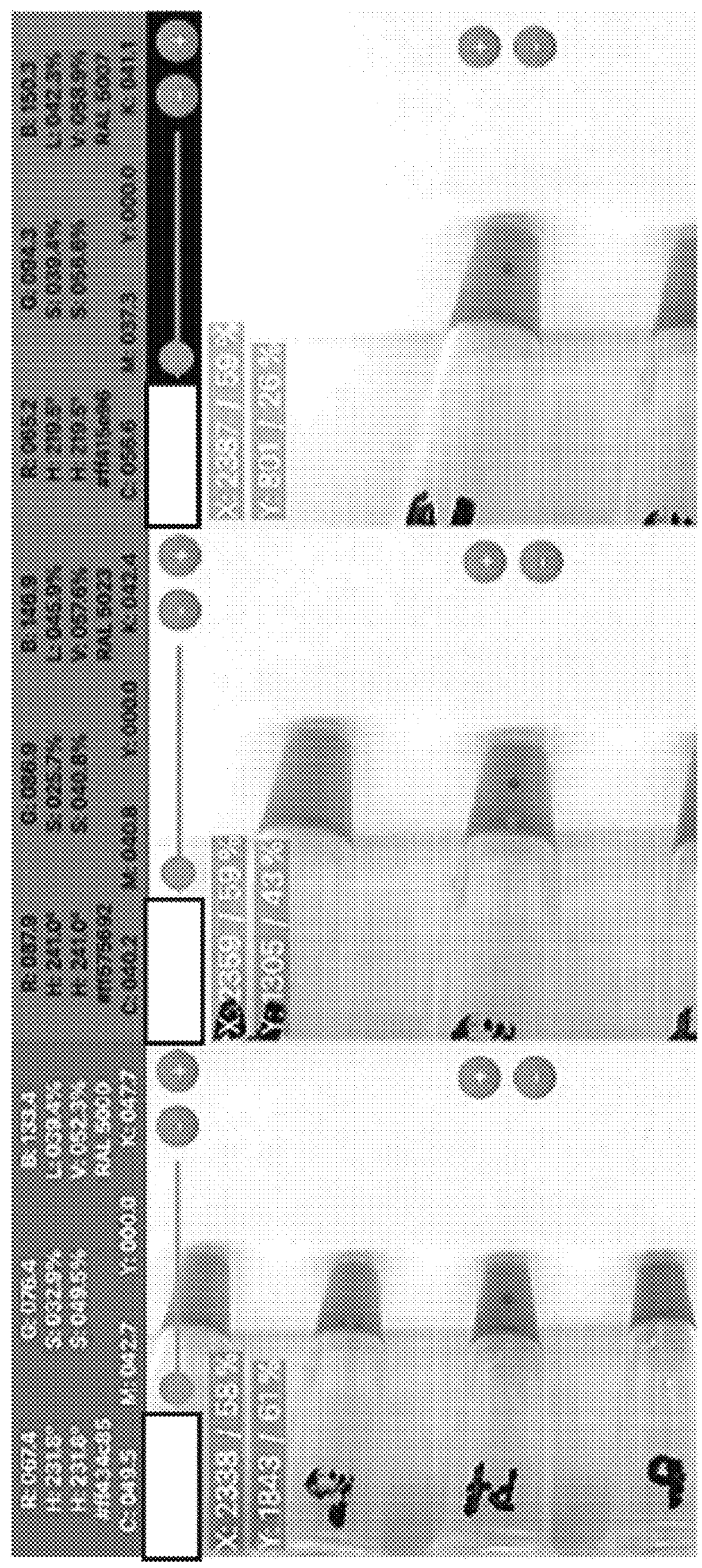
FIG. 3 illustrates the process of quantifying the color change of the reaction mixture using the RGB detector.

The present invention provides a multi-diagnostic kit for mosquito-borne diseases. The multi-diagnostic kit of the invention enables rapid and accurate detection of dengue virus and malaria parasites by using specific primer sets. The multi-diagnostic kit is applicable in regions with high incidences of mosquito-borne disease pandemics including Africa and Latin America since it exhibits excellent thermal stability even in harsh environments.

The reagent composition of the invention may include the followings:

(1) Primers: LAMP requires four to six primers to recognize six distinct regions on the target DNA. These include: Forward Inner Primer (FIP), Backward Inner Primer (BIP), Forward Outer Primer (F3), Backward Outer Primer (B3), Optional loop primers (LF and LB) to accelerate the reaction.

(2) DNA Polymerase: A strand-displacing DNA polymerase, such as Bst polymerase, which operates effectively at a constant temperature (60-65° C.) without the need for thermal cycling.

(3) dNTPs (Deoxynucleotide Triphosphates): The building blocks for DNA synthesis, including dATP, dTTP, dGTP, and dCTP, which are required for the polymerase to elongate the DNA strands.

(4) Buffer Solution: Typically includes Tris-HCl to maintain the optimal pH, as well as other salts like KCl and $MgSO_4$ (or $MgCl_2$) that stabilize the reaction environment and support enzyme activity.

(5) Betaine: used to reduce the formation of secondary structures in DNA, which can improve reaction efficiency and yield, especially in reactions with high GC content.

(6) Colorimetric Indicator: Indicators such as Hydroxy Naphthol Blue (HNB) or phenol red can be added to allow for visual detection of the amplification. When added, these indicators change color in response to changes in pH or ion concentration due to DNA synthesis, making it easy to observe results without electrophoresis.

(7) Template DNA: The sample DNA containing the target sequence to be amplified.

(8) Optional Additives: DMSO (dimethyl sulfoxide) or other additives can be used to improve reaction efficiency, especially with difficult templates.

The method for diagnosing dengue and malaria, including: adding DNA extracted from a sample to the reagent composition in the multi-diagnostic kit, and performing loop-mediated isothermal amplification of the DNA.

The loop-mediated isothermal amplification process includes: (i) binding of primers to target DNA, (ii) strand displacement and loop formation, (iii) cyclic amplification with inner and loop primers, and (iv) detection of amplification through visual, colorimetric, or fluorescent methods.

The invention provides a method for diagnosing dengue fever and malaria, the method including: (a) adding DNA extracted from a sample to a composition including a first primer set consisting of nucleotide sequences of SEQ ID Nos. 1 to 6 and a second primer set consisting of nucleotide sequences of SEQ ID Nos. 7 to 11; (b) performing a loop-mediated isothermal amplification (LAMP) reaction of the DNA to produce a colorimetric change; and (c) capturing an image of the reaction tube and analyzing the image using a trained artificial intelligence model to determine whether the reaction indicates a positive or negative result for Dengue virus or *Plasmodium falciparum.*

The composition may further include a third primer set consisting of the nucleotide sequences of SEQ ID Nos. 12 to 16, and wherein the analysis step additionally indicates whether a reaction result for *Plasmodium vivax* is positive or negative.

In one embodiment, the analysis step of the present invention is performed using an artificial intelligence (AI) model trained to classify colorimetric changes in the LAMP reaction tubes.

The AI model may be implemented using any known convolutional neural network (CNN) or equivalent deep learning architecture capable of image classification.

Examples of suitable architectures include MobileNetV3, EfficientNet, ResNet, or other functionally equivalent models.

The specific structure or implementation of the AI model is not limited to any particular algorithm, and any model capable of distinguishing positive and negative colorimetric outcomes based on image features may be employed.

The AI model receives, as input, an image of a LAMP reaction tube captured after the amplification reaction, and optionally metadata such as reaction time and temperature.

By analyzing visual information, including hue, saturation, brightness, and transparency of the reaction mixture, the AI model determines whether the reaction corresponds to a positive or negative result for Dengue virus, *Plasmodium falciparum*, or *Plasmodium vivax.*

This automated classification process allows objective and reproducible interpretation of colorimetric LAMP reactions without requiring visual inspection by a human operator.

In certain embodiments, the AI model may be executed on a local computing device such as a smartphone or tablet, or alternatively on a remote server through a cloud-based platform.

Captured images can be processed in standard color spaces such as RGB, HSV, or LAB to improve robustness under varying lighting conditions.

The diagnostic result may be displayed through a graphical user interface (GUI) that visually indicates infection status and, optionally, a confidence score representing the model's classification probability.

Preferably, the AI model is trained on a dataset containing labeled images of LAMP reaction tubes showing both positive and negative outcomes.

To ensure balanced learning performance, the dataset may include variations in illumination, temperature, and reaction time.

However, the specific training dataset, parameters, or algorithmic details are not essential to the practice of the invention, so long as the model is configured to automatically identify and classify colorimetric changes associated with the LAMP reaction.

The diagnostic method of the present invention is industrially applicable to various fields requiring rapid and accurate detection of mosquito-borne infectious diseases such as Dengue virus, *Plasmodium falciparum*, and *Plasmodium vivax.*

Because the method utilizes a colorimetric loop-mediated isothermal amplification (LAMP) reaction combined with automatic interpretation by an artificial-intelligence-based image analysis system, it can be implemented without the need for highly trained personnel or expensive analytical instruments.

The AI-assisted colorimetric analysis described herein can be integrated into portable diagnostic devices, smartphone-based readers, or cloud-connected laboratory information systems.

In one embodiment, a mobile application installed on a smartphone may capture an image of a LAMP reaction tube and analyze the image using an embedded or cloud-based AI model to determine the infection status within minutes.

The results can be displayed on a graphical user interface (GUI) showing "Positive" or "Negative" outcomes for each pathogen together with an optional confidence score.

This configuration enables decentralized testing in clinics, rural health centers, and field laboratories where access to conventional PCR instruments is limited.

Furthermore, the diagnostic kit of the invention can be mass-produced using standard reagent-formulation and packaging technologies.

Because the AI analysis is software-based, it can be distributed through digital platforms and easily updated to incorporate additional pathogen-specific primer sets.

Accordingly, the present invention provides a scalable and cost-effective diagnostic platform that can be adapted for a wide range of infectious disease monitoring programs, emergency response systems, and public health surveillance networks.

In addition, the ability of the AI model to objectively interpret color changes reduces inter-observer variability and enhances consistency across multiple testing sites.

Therefore, the LAMP-based diagnostic system of the present invention offers a significant industrial advantage in terms of accuracy, reproducibility, and accessibility, making it suitable for global deployment in both clinical and field environments.

Hereinafter, the invention is described in detail with reference to the following Examples.

EXAMPLE 1

1-1. Sample Acquisition and DNA Preparation

Plasmid DNA containing diagnostic gene regions for pathogens Dengue virus type 2 strain (DENV) was acquired from Gyeongsang National University College of Medicine in Korea, *P. falciparum*, and *P. vivax* were acquired from Gachon University College of Medicine in Korea. The DNA was extracted from infected blood samples, and the essential gene regions were cloned into a T&A cloning vector (T-vector). These T-vector-cloned plasmid DNAs were used in the experiments to identify and confirm the presence of pathogens DENV, *P. falciparum*, and *P. vivax*.

The lengths of the diagnostic gene regions are indicated in Table 1.

TABLE 1

| Pathogen | Gene Region Length (bp) |
|---|---|
| DENV | 511 |
| *P. falciparum* | 2,092 |
| *P. vivax* | 2,064 |

1-2. Primer Design for LAMP Assay

The T-vector was utilized to incorporate sequences of interest to enable specific and sensitive detection of diagnostic targets. LAMP primers were then designed for each diagnostic sequence within the T-vector. LAMP primers were designed using Primer Explorer V5. Sequences were aligned and analyzed using Clustal Omeg to ensure uniqueness and specificity.

The design criteria for the primers included a length of 18-25 nucleotides, a GC content of 40-60%, and melting temperatures (Tm) of 60-65° C. for outer primers and 55-60° C. for inner primers. Primer specificity was confirmed through in silico analysis using BLAS.

For each diagnostic sequence (DENV, *P. falciparum*, and *P. vivax*), the primer sets were designed as shown in Table 2, and the primer positions according to the sequences is provided in FIGS. 2A and 2B.

TABLE 2

| Target | Primer set | | | Sequence (5' -> 3') |
|---|---|---|---|---|
| Dengue virus type 2 | first primer set | outer primer | F3 | SEQ ID No. 1 |
| | | | B3 | SEQ ID No. 2 |
| | | inner primer | FIP | SEQ ID No. 3 |
| | | | BIP | SEQ ID No. 4 |
| | | loop primer | LF | SEQ ID No. 5 |
| | | | LB | SEQ ID No. 6 |
| *Plasmodium falciparum* | second primer set | outer primer | F3 | SEQ ID No. 7 |
| | | | B3 | SEQ ID No. 8 |
| | | inner primer | FIP | SEQ ID No. 9 |
| | | | BIP | SEQ ID No. 10 |
| | | loop primer | LF | SEQ ID No. 11 |
| *Plasmodium vivax* | third primer set | outer primer | F3 | SEQ ID No. 12 |
| | | | B3 | SEQ ID No. 13 |
| | | inner primer | FIP | SEQ ID No. 14 |
| | | | BIP | SEQ ID No. 15 |
| | | loop primer | LF | SEQ ID No. 16 |

1-3. Preparation of LAMP Buffer, Enzyme and LAMP Reaction

The LAMP reactions were performed in a total volume of 25 μL. The reaction mixture consisted of distilled water, 2.5 μL of 10×LAMP buffer, 1.4 mM of each deoxynucleotide triphosphate (dNTP), 8 U of Bst DNA polymerase (Enzynomics), 1.6 μM of each inner primer (FIP and BIP), 0.2 μM of each outer primer (F3 and B3), and 0.8 μM of each loop primer (LF and LB). The reaction mixes also included 0.8 M of betaine, 8 mM of magnesium sulfate ($MgSO_4$), and 120 μM of HNB as a colorimetric indicator. A 1 μL aliquot of the DNA template was added to each reaction.

To optimize the amplification conditions, the reaction mixtures were incubated at 65° C. for varying durations, specifically 0, 30, 45, 60, and 90 minutes. This step was essential to determine the optimal incubation time for the amplification process. Following optimization, the specificity of the LAMP assay was evaluated by incubating the reactions at 65° C. for 45 minutes, a duration selected based on preliminary optimization results.

Specificity experiments were conducted using a set of positive and negative controls. Positive controls consisted of reactions containing template DNA known to amplify under these conditions, while negative controls were reactions without template DNA to confirm the absence of non-specific amplification.

The LAMP buffer prepared for the amplification reaction was Thermopol buffer. The components of a 10× Thermopol buffer included 2 mL of 200 mM Tris-HCl, 1 mL of 100 mM $(NH_4)_2SO_4$, 1 mL of 100 mM KCl, 100 μL of 1% Triton® X-100 with pH 8.8 at 25° C., and 6.9 mL of water. The mixture was filtered using 0.2 μm syringe filter, resulting in 10 mL of Thermopol buffer.

The presence of amplification was determined visually based on the color change of HNB, with the color transition from purple to blue indicating a positive reaction. In cases where further confirmation was required, the products were analyzed by gel electrophoresis to verify the amplified fragments.

1-4. Agarose Gel Running

In order to run gel electrophoresis, 1.5× agarose gels were made. The agarose gel was prepared by weighing the agarose LE Master powder and mixing it with 100 mL of 1.5×TAE electrophoresis buffer in a flask. The agarose was dissolved by heating the mixture with a microwave until the solution was clear.

After cooling down the boiled solution, 120 μL of gel stain were added. The mixture was poured into the gel mold and left to dry.

1-5. RGB Detector

The application ColorDetector was employed to detect color differences over time following the reaction. The application provided the name of the detected color, along with the values of red, blue, and green, as well as hue, saturation, and lightness (HSL), saturation and value (HSV), and the proportions of cyan, magenta, yellow, and black (CMYK). This application was used to analyze the colors of HNB in the samples after the LAMP reactions.

1-6. Results (1) Plasmid DNA Sample Verification

Figure 4A:
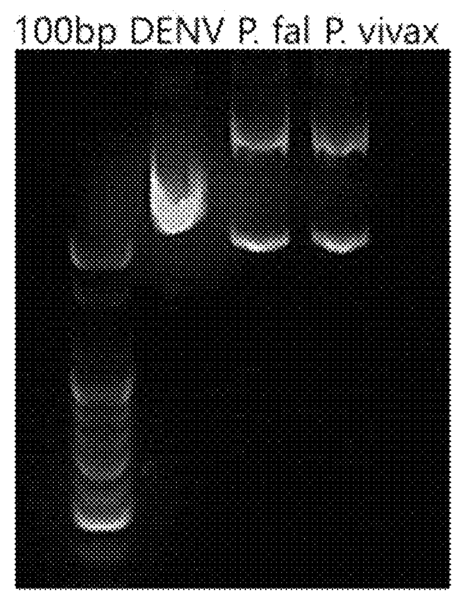
FIGS. 4A and 4B present the results of plasmid DNA gel electrophoresis and PCR amplification.
Figure 4B:
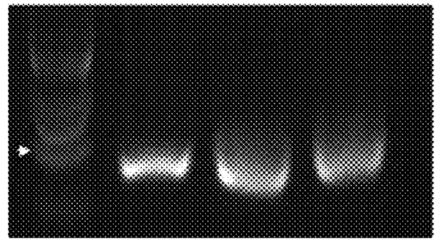

The three plasmid DNA samples were first verified by running them on an agarose gel (FIG. 4A). Following this, conventional PCR was performed using the designed LAMP outer primers under the following conditions: initial denaturation at 95° C. for 5 minutes, followed by 35 cycles of denaturation at 95° C. for 30 seconds, annealing at 58° C. for 30 seconds, and extension at 72° C. for 1 minute, with a final extension at 72° C. for 5 minutes. The results are presented in FIG. 4B.

(2) Analysis of Primer Specificity

Figure 5:
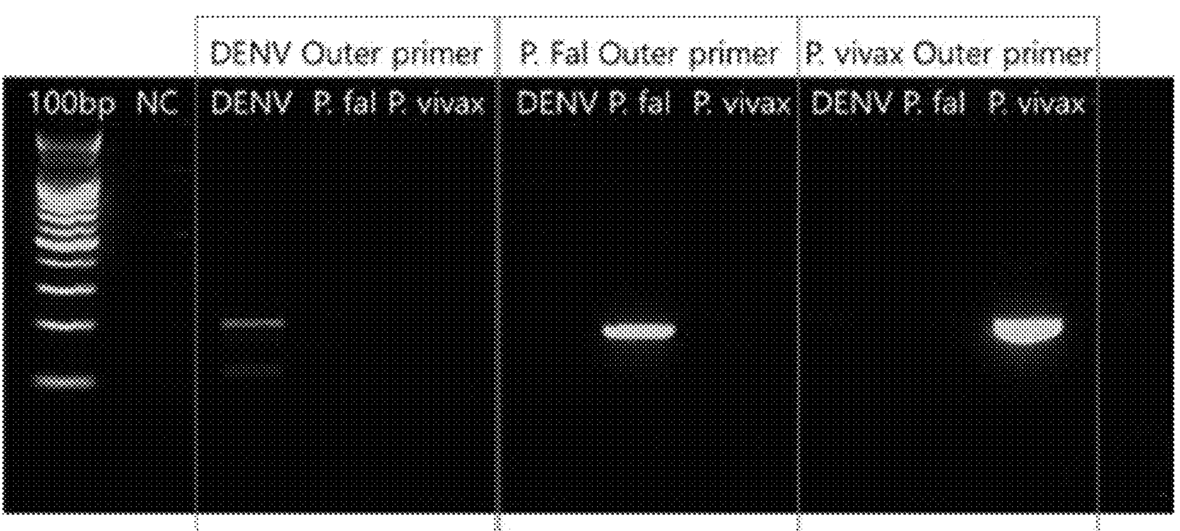
FIG. 5 shows an analysis of primer specificity in a cross-PCR experiment, where primers specific for DENV, *P. falciparum* (P. fal), and *P. vivax* were used to amplify DNA from corresponding plasmid templates. The PCR products were then loaded onto a 1.5% agarose gel for electrophoresis, demonstrating the specificity of each primer set for its target DNA.

Each plasmid DNA was amplified using its corresponding outer primer, and the PCR results demonstrated successful and specific amplification for each template. The specificity was confirmed by electrophoresis analysis presented in FIG. 5, where distinct bands corresponding to the expected sizes were observed, validating the precision of each primer set.

(3) Dye Color Change According to Solution

The color changes of the HNB dye when mixed with various reagents used in this experiment. The tubes display the dye's color response to each reagent adding, illustrating how the HNB dye reacts under different experimental conditions.

Figure 6:
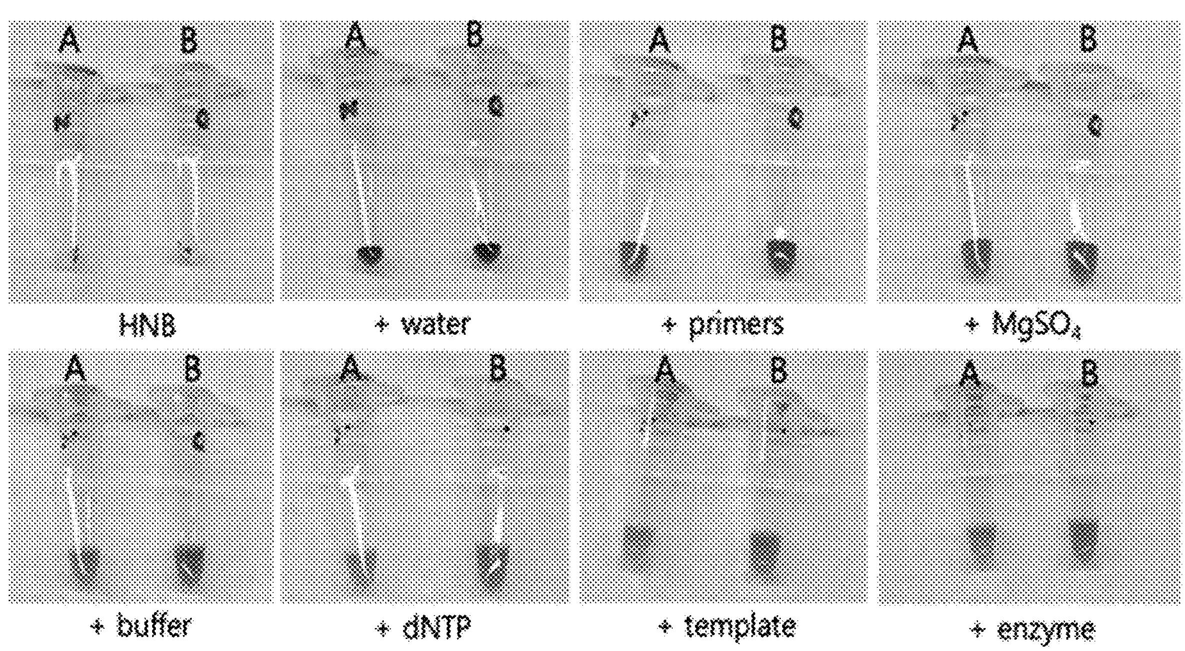
FIG. 6 shows results of HNB dye color changes in response to reagent compositions.

The visual color changes in the dye indicate its interaction with each reagent, providing insights into the chemical environment or conditions present in each case. FIG. 6 shows the sequential color changes of HNB dye observed as different solutions were added.

As shown in FIG. 6, each reagent addition caused a distinct color shift, indicating the progress of the reaction and enabling visual monitoring at each stage. This supports that HNB dye in the reagent composition of the present invention allows for effective visual assessment of DNA amplification through color change.

(4) Impact of Betaine Presence on LAMP Results

Figure 7A:
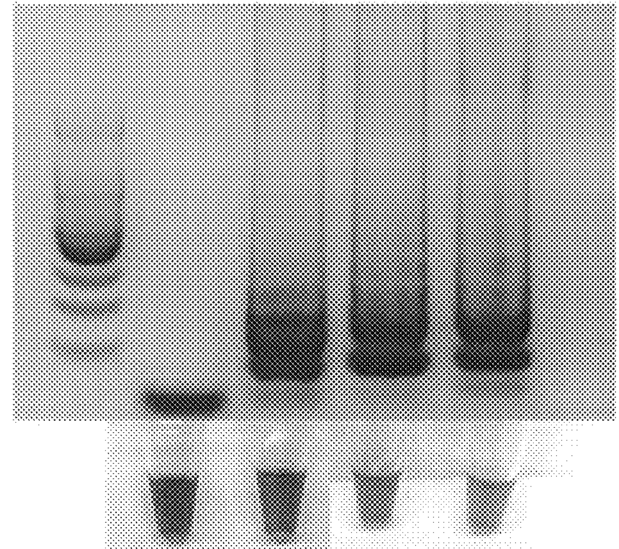
FIGS. 7A and 7B show the color change observed in the LAMP reaction with and without betaine.
Figure 7B:
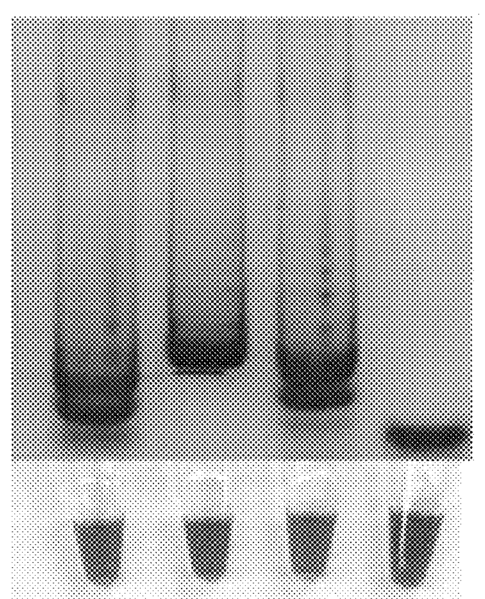

In the LAMP reaction, the effect of betaine on the stability of color change was investigated when using HNB as an indicator. Experiments were performed with and without the addition of betaine. The addition of betaine resulted in a more stable and consistent color change compared to the reactions without betaine as shown FIG. 7B. Additionally, the results were further confirmed by 1.5% agarose gel electrophoresis, which demonstrated the expected amplification patterns corresponding to the presence of betaine (FIG. 7A).

(5) Optimization of LAMP Reaction Time

For the time-dependent analysis of the LAMP reaction, 1 ng of template DNA was used in each reaction. The reactions were observed at intervals of 30, 45, 60, and 90 minutes. A slight color change was noted at around 30 minutes, with a more distinct and observable change at 45 minutes. The color remained stable for up to 60 minutes. Accordingly, an optimal LAMP reaction time for DENV, *P. falciparum*, and *P. vivax* is 30 to 60 minutes, and preferably 40 to 50 minutes.

(6) Optimization of DNA Template Concentration

The time course and sensitivity analysis of the LAMP assay for detecting DENV, *P. falciparum*, and *P. vivax* was performed using a range of target DNA concentrations (10 ng to 1 fg). Reactions were monitored at 0, 30, 45, 60, and 90 minutes, with amplification indicated by a color change from purple to blue. Negative controls (NC) were included in each set.

Figure 8A:
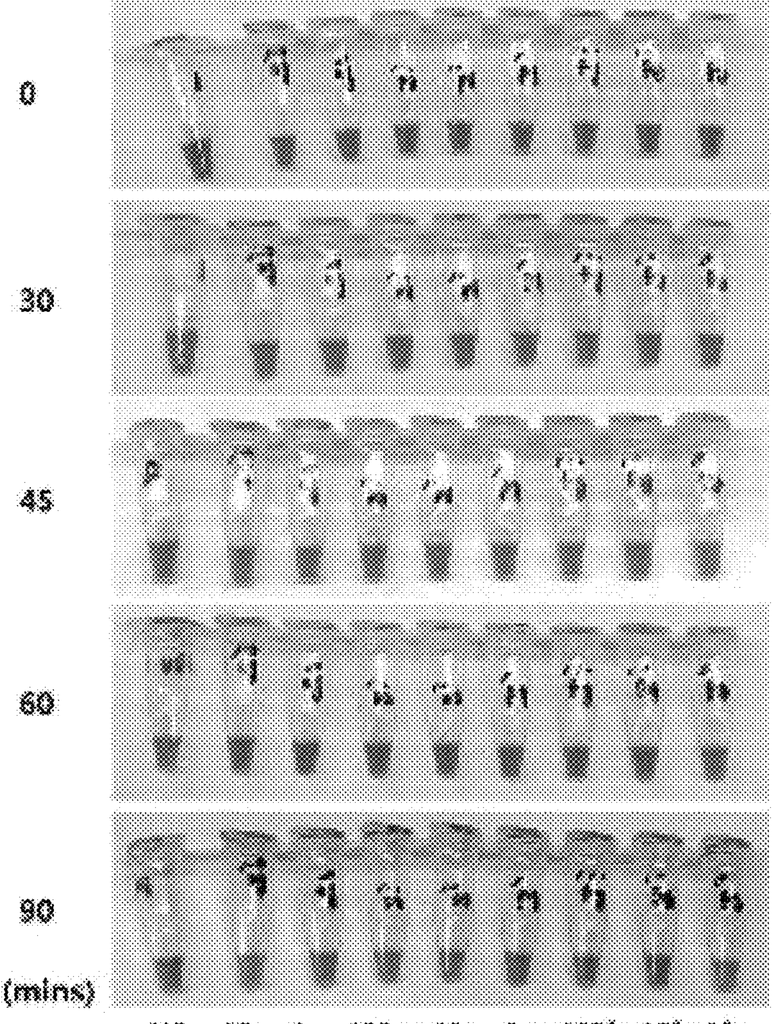
FIGS. 8A to 8C show the time-course and sensitivity analysis of the LAMP assay. Assays for DENV, *P. falciparum*, and *P. vivax* were conducted using DNA concentrations ranging from 10 ng to 1 fg. Reactions were monitored at 0, 30, 45, 60, and 90 minutes, with a color change from purple to blue indicating successful amplification.
Figure 8B:
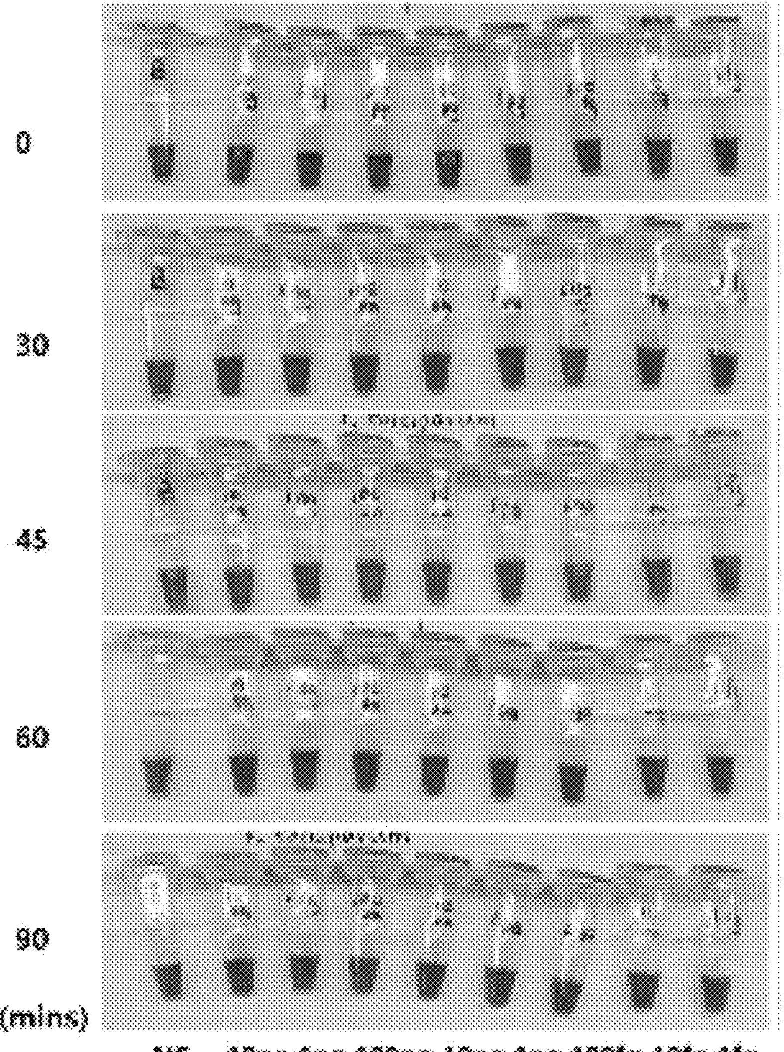
Figure 8C:
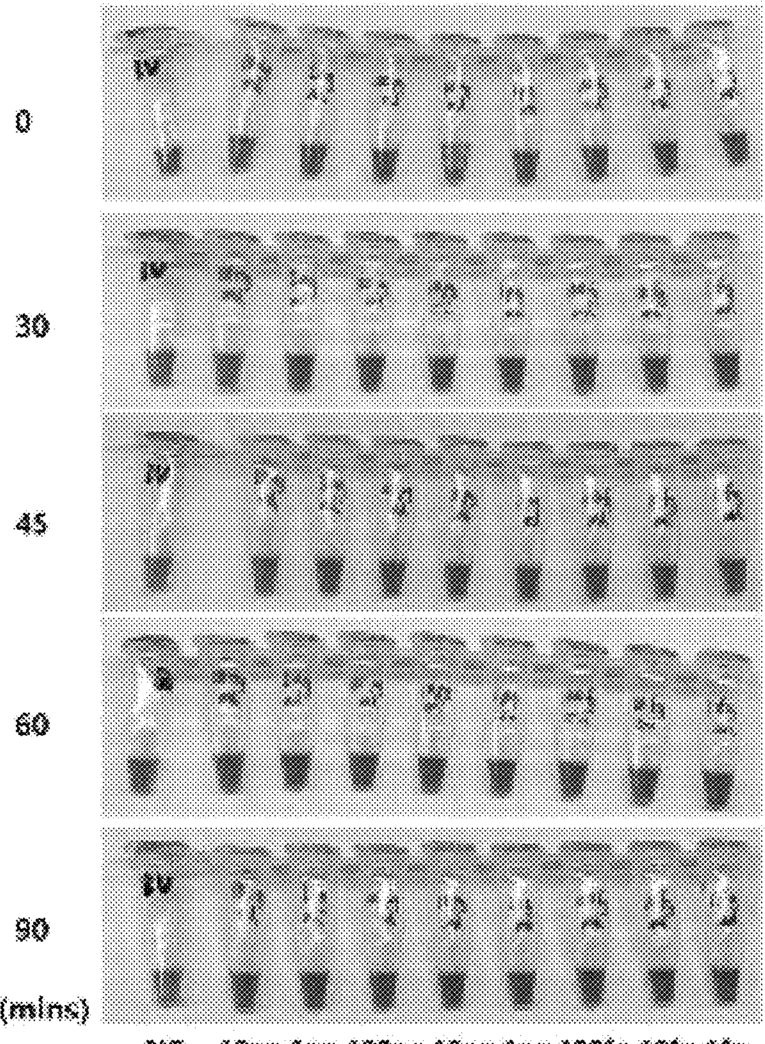
Figure 9A:
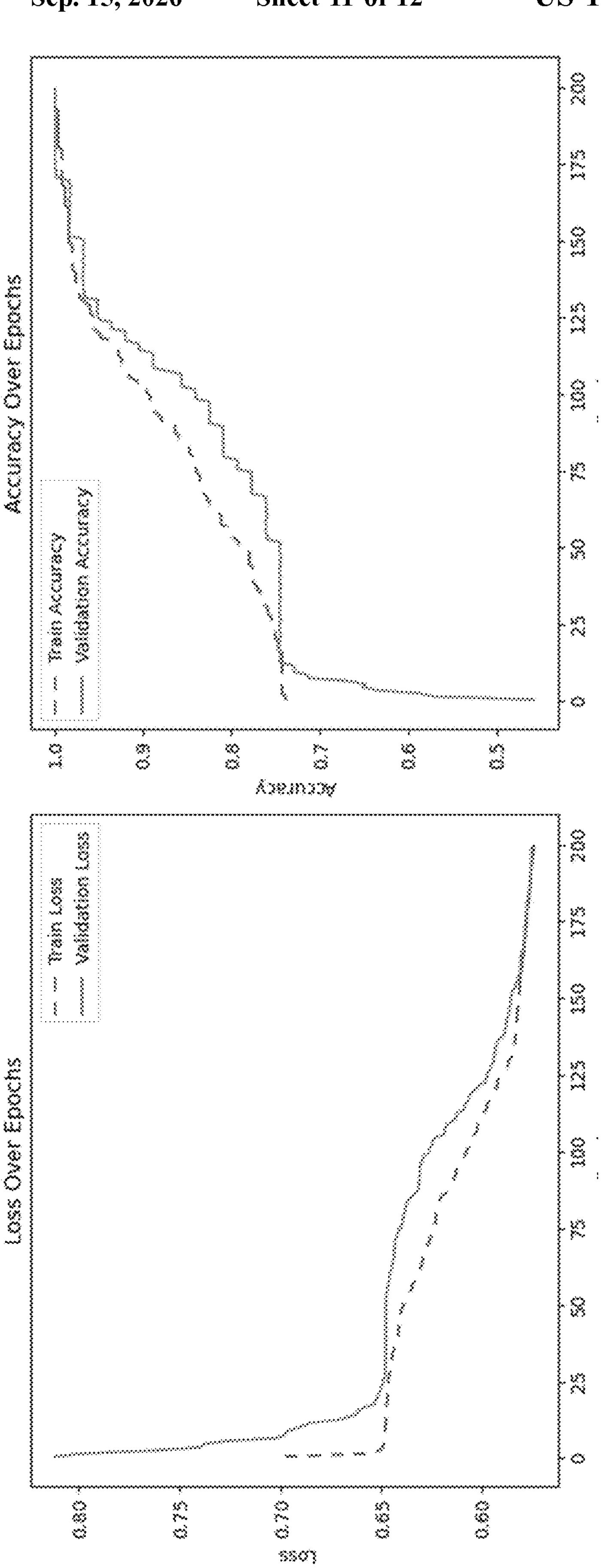
FIG. 9A shows loss and accuracy curves over training epochs for both training and validation datasets.
Figure 9B:
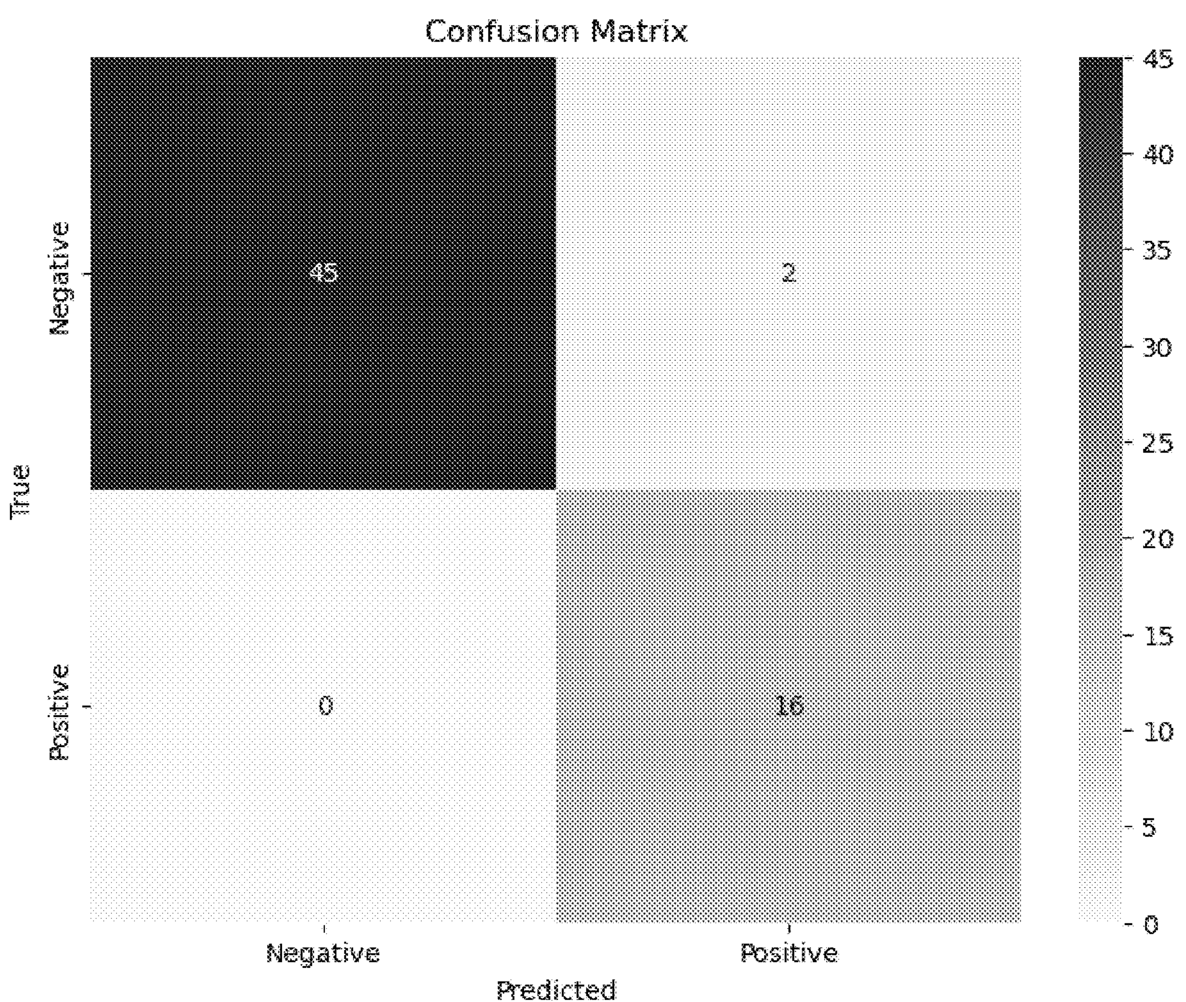
FIG. 9B is confusion matrix showing the distribution of true and predicted labels for the validation dataset.

For DENV, amplification occurred within 45 minutes for 10 μg and higher DNA concentrations. In the case of *P. falciparum*, positive results were observed after 45 minutes at concentrations of 10 μg and above. For *P. vivax*, amplification was detected at concentrations as low as 1 pg, with results appearing after 30 minutes. This time-course analysis highlights the sensitivity of the LAMP assay, demonstrating its ability to detect low concentrations of DNA from these pathogens at different time points (FIG. 8A to 8C).

The optimal (minimum) DNA template concentration for each pathogen in the LAMP reaction is shown in Table 3.

TABLE 3

| Pathogen | DNA template concentration (pg) | Reaction Time (min) |
|---|---|---|
| DENV | 10 | 45 |
| *P. falciparum* | 10 | 45 |
| *P. vivax* | 1 | 30 |

EXAMPLE 2

In this example, a trained artificial intelligence (AI) model was employed to automatically classify the outcomes of loop-mediated isothermal amplification (LAMP) reactions based on test tube images and reaction metadata.

The purpose of this experiment was to verify the feasibility of using an existing trained AI program to accurately determine positive and negative results from the colorimetric changes observed during the LAMP process.

2-1. Methods and Materials

The study utilized a dataset including a total of 312 images of LAMP reaction tubes for detection of DENV. Each image was paired with metadata including (i) the elapsed time since the initiation of the LAMP reaction (ranging from 0 to 90 minutes) and (ii) the reaction temperature (42° C., 55° C., or 65° C.). Each sample was assigned a binary label indicating whether the reaction was Positive or Negative.

To ensure that the diagnostic system was robust to environmental variations, image preprocessing and augmentation were performed prior to inference. The images were resized to 128×128 pixels, and data augmentation such as random horizontal flipping, rotation, and slight color jittering was applied to simulate real-world variability in lighting and viewing angle. The validation dataset was resized without augmentation to maintain evaluation consistency.

An artificial-intelligence-based classification model, previously trained using a convolutional neural network (CNN) architecture (MobileNetV3-based), was employed in this experiment. The model had been trained externally using a dataset of labeled LAMP tube images to distinguish positive from negative reactions based on colorimetric features. The model used in this example was not newly developed but was applied as an analytical tool to verify its ability to correctly interpret the color changes occurring in the present LAMP diagnostic compositions.

The trained model received both the LAMP tube image and the corresponding metadata (time and temperature) as input and produced a probability value between 0 and 1, indicating the likelihood of a positive reaction.

Model inference was conducted using Python and PyTorch (version 2.5) on a standard computing environment.

No retraining or modification of the neural network parameters was performed; rather, the trained AI program was used directly to process new reaction images generated according to the present invention's diagnostic compositions and reaction conditions.

2-2. Results

The applied AI program demonstrated excellent classification performance in distinguishing positive and negative LAMP reactions.

FIG. 1 shows the training and validation loss curves corresponding to the AI model's prior learning process. When applied to the present LAMP reaction images, the model exhibited stable inference behavior with no indication of overfitting.

The validation accuracy consistently converged near 100%, confirming the generalization capability of the pre-trained model when applied to new data produced by the diagnostic compositions described in this invention.

A confusion matrix generated from the validation dataset (FIG. 2) showed that the model correctly identified 45 out of 47 negative samples and 16 out of 16 positive samples, misclassifying only two negative samples as positive.

All positive samples were accurately detected. This result indicates strong sensitivity for detecting true positive reactions and excellent overall classification reliability.

Further evaluation using standard classification metrics confirmed the model's performance: precision was 1.00 for the negative class and 0.89 for the positive class, recall was 0.96 for the negative class and 1.00 for the positive class, and the overall accuracy reached 97%. The F1-scores were 0.98 for negative and 0.94 for positive reactions, indicating balanced performance between sensitivity and specificity.

This example demonstrates that an externally trained AI model can be effectively applied to the LAMP-based diagnostic method of the present invention to automatically classify colorimetric reaction outcomes.

The integration of elapsed time and temperature data was found to enhance diagnostic accuracy compared with image-only analysis, indicating that these parameters provide valuable contextual information for AI-based interpretation.

What is claimed is:

1. A method for diagnosing dengue fever and malaria, the method comprising:

adding DNA extracted from a sample to a composition comprising a first primer set consisting of nucleotide sequences of SEQ ID Nos. 1 to 6 and a second primer set consisting of nucleotide sequences of SEQ ID Nos. 7 to 11 in a reaction tube;

performing a loop-mediated isothermal amplification (LAMP) reaction of the DNA in the reaction tube to produce a colorimetric change; and capturing an image of the reaction tube and analyzing the image using a trained artificial intelligence model to determine whether the reaction indicates a positive or negative result for Dengue virus or *Plasmodium falciparum*.

2. The method according to claim 1, wherein the composition further comprises a third primer set consisting of the nucleotide sequences of SEQ ID Nos. 12 to 16, and the analyzing indicates whether a reaction result for *Plasmodium vivax* is positive or negative.

3. The method according to claim 1, wherein the composition further comprises hydroxy naphthol blue (HNB).

4. The method according to claim 1, wherein the composition further comprises betaine.

5. The method according to claim 1, wherein the amplification reaction is carried out at 60 to 65° C. for 0.5 to 1 hour.

6. The method according to claim 1, wherein the sample is blood, saliva, urine, and/or tissue.

7. The method according to claim 1, wherein the artificial intelligence model is a convolutional neural network trained on labeled images of positive and negative colorimetric reactions.

8. The method according to claim 1, wherein the captured image is analyzed in RGB (red, green, blue), HSV (hue, saturation, value), or LAB (lightness, a, and b) color space.

9. The method according to claim 1, wherein the positive or negative result is displayed via a graphical user interface indicating infection status for each pathogen.

10. The method according to claim 1, wherein the artificial intelligence model provides a confidence score representing the probability of infection.

11. The method according to claim 1, wherein the image is captured using a mobile device camera and analyzed locally or through a cloud-based server.

* * * * *

SEQUENCE LISTING

```
Sequence total quantity: 19
SEQ ID NO: 1           moltype = DNA  length = 20
FEATURE                Location/Qualifiers
misc_feature           1..20
                       note = F3 for Dengue
source                 1..20
                       mol_type = other DNA
                       organism = synthetic construct
SEQUENCE: 1
cgttccattt aaccacacgt                                              20

SEQ ID NO: 2           moltype = DNA  length = 20
FEATURE                Location/Qualifiers
misc_feature           1..20
                       note = B3 for Dengue
source                 1..20
                       mol_type = other DNA
                       organism = synthetic construct
SEQUENCE: 2
gcaccaacag tctatgtctt                                              20

SEQ ID NO: 3           moltype = DNA  length = 41
FEATURE                Location/Qualifiers
misc_feature           1..41
                       note = FIP for Dengue
source                 1..41
                       mol_type = other DNA
                       organism = synthetic construct
SEQUENCE: 3
catgttcacg ccatcctctg ttggagaacc acacatgatc g                      41

SEQ ID NO: 4           moltype = DNA  length = 39
FEATURE                Location/Qualifiers
misc_feature           1..39
                       note = BIP for Dengue
source                 1..39
                       mol_type = other DNA
                       organism = synthetic construct
SEQUENCE: 4
cctcatggcc atggaccttg gctcattctg cctgagaag                         39
```

```
SEQ ID NO: 5            moltype = DNA  length = 25
FEATURE                 Location/Qualifiers
misc_feature            1..25
                        note = LF for Dengue
source                  1..25
                        mol_type = other DNA
                        organism = synthetic construct
SEQUENCE: 5
cttttccctt tctcttgtct gctga                                       25

SEQ ID NO: 6            moltype = DNA  length = 24
FEATURE                 Location/Qualifiers
misc_feature            1..24
                        note = LB for Dengue
source                  1..24
                        mol_type = other DNA
                        organism = synthetic construct
SEQUENCE: 6
gacacaatca cgtacaagtg tccc                                        24

SEQ ID NO: 7            moltype = DNA  length = 21
FEATURE                 Location/Qualifiers
misc_feature            1..21
                        note = F3 for P. falciparum
source                  1..21
                        mol_type = other DNA
                        organism = synthetic construct
SEQUENCE: 7
gcatttgtct aaaatacttc c                                           21

SEQ ID NO: 8            moltype = DNA  length = 18
FEATURE                 Location/Qualifiers
misc_feature            1..18
                        note = B3 for P. falciparum
source                  1..18
                        mol_type = other DNA
                        organism = synthetic construct
SEQUENCE: 8
cgaatactcg ccccagaa                                               18

SEQ ID NO: 9            moltype = DNA  length = 49
FEATURE                 Location/Qualifiers
misc_feature            1..49
                        note = FIP for P. falciparum
source                  1..49
                        mol_type = other DNA
                        organism = synthetic construct
SEQUENCE: 9
acctagtcgg catagtttat ggttataatc aagaacgaaa gttaaggga             49

SEQ ID NO: 10           moltype = DNA  length = 47
FEATURE                 Location/Qualifiers
misc_feature            1..47
                        note = BIP for P. falciparum
source                  1..47
                        mol_type = other DNA
                        organism = synthetic construct
SEQUENCE: 10
agtcatcttt cgaggtgact tttagcccaa agactttgat ttctcat               47

SEQ ID NO: 11           moltype = DNA  length = 23
FEATURE                 Location/Qualifiers
misc_feature            1..23
                        note = LF for P. falciparum
source                  1..23
                        mol_type = other DNA
                        organism = synthetic construct
SEQUENCE: 11
cgacggtatc tgatcgtctt cac                                         23

SEQ ID NO: 12           moltype = DNA  length = 21
FEATURE                 Location/Qualifiers
misc_feature            1..21
                        note = F3 for P. vivax
source                  1..21
                        mol_type = other DNA
                        organism = synthetic construct
SEQUENCE: 12
```

```
tcgtgaatat gatttgtctg g                                          21

SEQ ID NO: 13          moltype = DNA  length = 20
FEATURE                Location/Qualifiers
misc_feature           1..20
                       note = B3 for P. vivax
source                 1..20
                       mol_type = other DNA
                       organism = synthetic construct
SEQUENCE: 13
agcaaataca ttcttacgcg                                            20

SEQ ID NO: 14          moltype = DNA  length = 47
FEATURE                Location/Qualifiers
misc_feature           1..47
                       note = FIP for P. vivax
source                 1..47
                       mol_type = other DNA
                       organism = synthetic construct
SEQUENCE: 14
tcagtcccac gtaagaatat atcgtttaat tccgataacg aacgaga              47

SEQ ID NO: 15          moltype = DNA  length = 47
FEATURE                Location/Qualifiers
misc_feature           1..47
                       note = BIP for P. vivax
source                 1..47
                       mol_type = other DNA
                       organism = synthetic construct
SEQUENCE: 15
tattgggata cgtaacagtt tcccaagaaa cagtatgaaa agcgaac              47

SEQ ID NO: 16          moltype = DNA  length = 25
FEATURE                Location/Qualifiers
misc_feature           1..25
                       note = LF for P. vivax
source                 1..25
                       mol_type = other DNA
                       organism = synthetic construct
SEQUENCE: 16
atttgccgct aattagcagg ttaag                                      25

SEQ ID NO: 17          moltype = DNA  length = 224
FEATURE                Location/Qualifiers
source                 1..224
                       mol_type = genomic DNA
                       organism = Dengue virus
SEQUENCE: 17
attccaacag tgatggcgtt ccatttaacc acacgtaacg gagaaccaca catgatcgtc  60
agcagacaag agaaagggaa aagtcttctg tttaaaacag aggatggcgt gaacatgtgt  120
accctcatgg ccatggacct tggtgaattg tgtgaagaca caatcacgta caagtgtccc  180
cttctcaggc agaatgagcc agaagacata gactgttggt gcaa                 224

SEQ ID NO: 18          moltype = DNA  length = 228
FEATURE                Location/Qualifiers
source                 1..228
                       mol_type = genomic DNA
                       organism = Plasmodium falciparum
SEQUENCE: 18
tgcgaaagca tttgtctaaa atacttccat taatcaagaa cgaaagttaa gggagtgaag  60
acgatcagat accgtcgtaa tcttaaccat aaactatgcc gactaggtgt tggatgaaag  120
tgttaaaaat aaaagtcatc tttcgaggtg acttttagat tgcttccttc agtaccttat  180
gagaaatcaa agtctttggg ttctggggcg agtattcgcg caagcgag             228

SEQ ID NO: 19          moltype = DNA  length = 227
FEATURE                Location/Qualifiers
source                 1..227
                       mol_type = genomic DNA
                       organism = Plasmodium vivax
SEQUENCE: 19
ttagttcgtg aatatgattt gtctggttaa ttccgataac gaacgagatc ttaacctgct  60
aattagcggc aaatacgata tattcttacg tgggactgaa ttcggttgat ttgcttactt  120
cgaagaaaat attgggatac gtaacagttt ccctttccct tttctactta gttcgctttt  180
catactgttt ctttttcgcg taagaatgta tttgcttagt tgtaaag              227
```